（12) United States Patent
Sumanasinghe

(10) Patent No.: US 11,278,391 B2
(45) Date of Patent: Mar. 22, 2022

(54) GRAFT HAVING AT LEAST ONE WOVEN TAPER

(71) Applicant: Cook Medical Technologies LLC, Bloomington, IN (US)

(72) Inventor: Ruwan Sumanasinghe, Carmel, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 146 days.

(21) Appl. No.: 16/553,394

(22) Filed: Aug. 28, 2019

(65) Prior Publication Data

US 2020/0069411 A1 Mar. 5, 2020

Related U.S. Application Data

(60) Provisional application No. 62/725,097, filed on Aug. 30, 2018.

(51) Int. Cl.
*A61F 2/07* (2013.01)
*A61F 2/06* (2013.01)

(52) U.S. Cl.
CPC .......... *A61F 2/07* (2013.01); *A61F 2002/065* (2013.01); *A61F 2240/001* (2013.01); *D10B 2509/06* (2013.01)

(58) Field of Classification Search
CPC ............................. A61F 2/07; A61F 2002/065
See application file for complete search history.

(56) References Cited

U.S. PATENT DOCUMENTS

| | | | |
|---|---|---|---|
| 6,280,467 B1 | 8/2001 | Leonhardt | |
| 6,475,232 B1 | 11/2002 | Babbs et al. | |
| 6,626,938 B1 | 9/2003 | Butaric et al. | |
| 6,994,724 B2 | 2/2006 | Schmitt | |
| 7,122,052 B2 | 10/2006 | Greenhalgh | |
| 7,226,474 B2 | 6/2007 | Iancea et al. | |
| 7,550,004 B2 | 6/2009 | Bahler et al. | |
| 7,582,110 B2 | 9/2009 | Case et al. | |
| 7,758,626 B2 | 7/2010 | Kim et al. | |
| 8,287,586 B2 | 10/2012 | Schaeffer et al. | |
| 8,696,733 B2 | 4/2014 | Bogert et al. | |
| 9,427,306 B2 | 8/2016 | Shahriari | |
| 9,827,086 B2 | 11/2017 | Winner et al. | |
| 2002/0058991 A1* | 5/2002 | Schmitt .................... | A61F 2/06 623/1.15 |
| 2005/0154446 A1 | 7/2005 | Phillips et al. | |
| 2013/0184808 A1 | 7/2013 | Hall et al. | |

(Continued)

*Primary Examiner* — Suba Ganesan
(74) *Attorney, Agent, or Firm* — Crowell & Moring LLP

(57) ABSTRACT

An implantable graft may include a main section having walls formed with a woven fabric, the main section having a main lumen extending therethrough. The implantable graft may also include a bifurcated section having walls formed with the woven fabric, where the bifurcated section extends from main section, where the bifurcated section includes a first branch and a second branch, and where the first branch and the second branch each include a branch lumen in fluid communication with the main lumen. At least one branch of the bifurcated section may include a branch taper formed by a seam connecting a first woven layer and a second woven layer. A seam extension may extend outwardly along the seam of the branch taper, the seam extension being a single-layer woven structure.

20 Claims, 6 Drawing Sheets

(56) References Cited

U.S. PATENT DOCUMENTS

2015/0342721 A1\* 12/2015 Winner ................... A61F 2/06
623/1.51
2017/0105854 A1 4/2017 Treacy et al.

\* cited by examiner

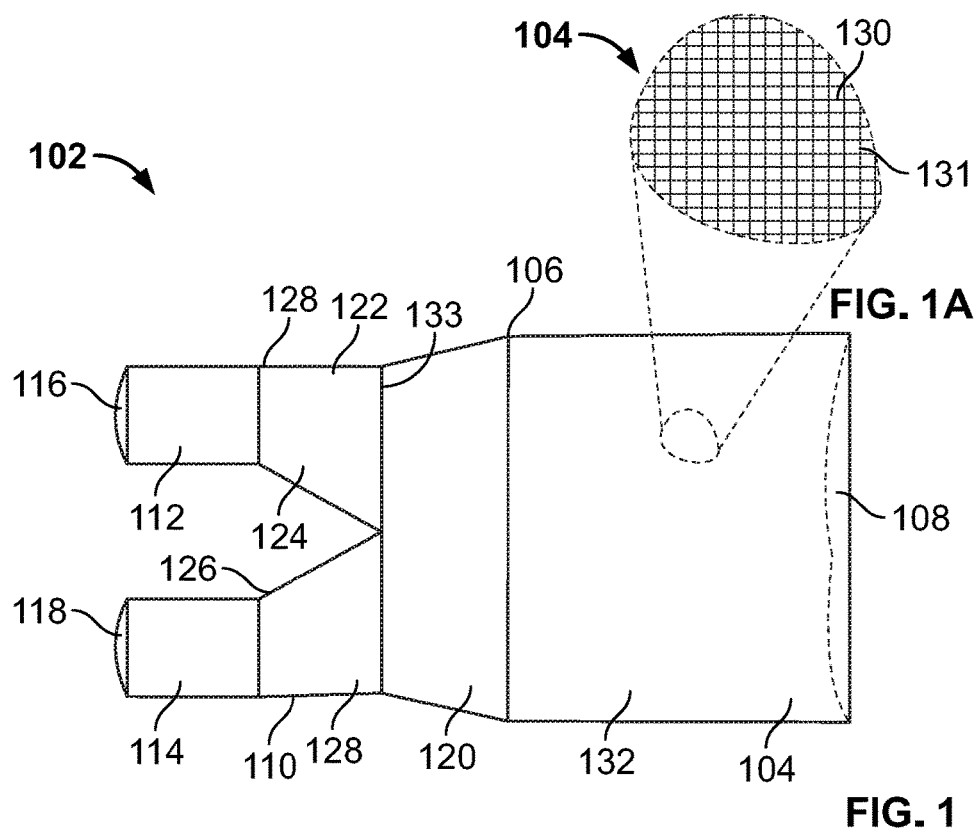
FIG. 1A
FIG. 1
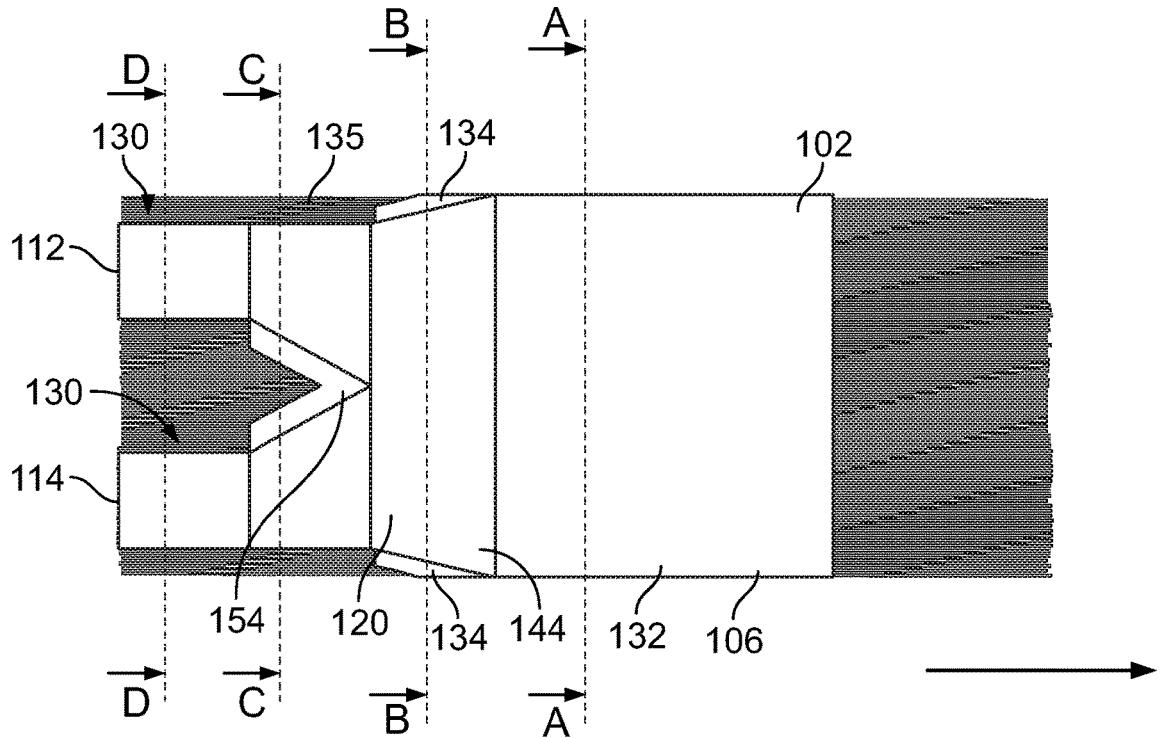
FIG. 2

GRAFT HAVING AT LEAST ONE WOVEN TAPER

RELATED APPLICATIONS

This application claims the benefit of U.S. Provisional Application No. 62/725,097, filed Aug. 30, 2018, which is hereby incorporated by reference in its entirety.

BACKGROUND

Aneurysms occur in blood vessels in locations where, due to age, disease or genetic predisposition, the blood vessel strength or resiliency is insufficient to enable the blood vessel wall to retain its shape as blood flows therethrough, resulting in a ballooning or stretching of the blood vessel at the limited strength/resiliency location to thereby form an aneurysmal sac. If the aneurysm is left untreated, the blood vessel wall may continue to expand, to the point where the remaining strength of the blood vessel wall is below that necessary to prevent rupture, and the blood vessel will fail at the aneurysm location, often with fatal result.

To prevent rupture, a stent graft of a tubular construction may be introduced into the blood vessel, for example intraluminally. Typically, the stent graft is deployed and secured in a location within the blood vessel such that the stent graft spans the aneurysmal sac. The outer surface of the stent graft, at its opposed ends, is sealed to the interior wall of the blood vessel at a location where the blood vessel wall has not suffered a loss of strength or resiliency. Blood flow in the vessel is thus channeled through the hollow interior of the stent graft, thereby reducing, if not eliminating, any stress on the blood vessel wall at the aneurysmal sac location. Therefore, the risk of rupture of the blood vessel wall at the aneurysmal location is significantly reduced, if not eliminated, and blood can continue to flow through to the downstream blood vessels without interruption.

Woven fabrics are useful in the construction of grafts due to their desirable mechanical properties and the ease and low cost of manufacturing such fabrics. However, existing woven fabrics cannot include certain shapes, such as tapers, without compromising the structural integrity of such fabrics (e.g., due to the potential for fraying). In view of this background, the present disclosure provides an improved woven graft material for use in a stent graft.

BRIEF SUMMARY

In one aspect, an implantable graft may include a main section having walls formed with a woven fabric, the main section having a main lumen extending therethrough. The implantable graft may also include a bifurcated section having walls formed with the woven fabric, where the bifurcated section extends from main section, where the bifurcated section includes a first branch and a second branch, and where the first branch and the second branch each include a branch lumen in fluid communication with the main lumen. At least one branch of the bifurcated section may include a branch taper formed by a seam connecting a first woven layer and a second woven layer. A seam extension may extend outwardly along the seam of the branch taper, the seam extension being a single-layer woven structure.

In another aspect, an implantable graft may include a woven fabric forming walls of a first tubular section and a second section, the first tubular section having a first diameter and the second section having a smaller second diameter. A tapered section located between the first tubular section and the second section may decreases in diameter as it extends from the first tubular section to the second section. A seam extension extending from a seam of the tapered section may join a first woven layer of the tapered section to a second woven layer of the tapered section. The seam extension may include a single-layer woven structure.

In another aspect, the present disclosure provides a method of weaving an implantable graft. The implantable graft may include a main section having walls formed with a woven fabric, the main section having a main lumen extending therethrough. The implantable graft may also include a bifurcated section having walls formed with the woven fabric, where the bifurcated section extends from main section, where the bifurcated section includes a first branch and a second branch, and where the first branch and the second branch each include a branch lumen in fluid communication with the main lumen. At least one branch of the bifurcated section may include a branch taper formed by a seam connecting a first woven layer and a second woven layer. A seam extension may extend outwardly along the seam of the branch taper, the seam extension being a single-layer woven structure.

BRIEF DESCRIPTION OF THE DRAWINGS

The embodiments will be further described in connection with the attached drawings. It is intended that the drawings included as a part of this specification be illustrative of the exemplary embodiments and should in no way be considered as a limitation on the scope of the present disclosure. Indeed, the present disclosure specifically contemplates other embodiments not illustrated but intended to be included in the claims.

FIG. 1 is an illustration showing a woven graft in accordance with certain aspects of the present disclosure.

FIG. 1A is an illustration showing a magnified view of a woven fabric forming at least a portion of the woven graft of FIG. 1 in accordance with certain aspects of the present disclosure.

FIG. 2 is an illustration showing a diagram of a weaving orientation during formation of the graft of FIG. 1 in accordance with certain aspects of the present disclosure.

DETAILED DESCRIPTION

Figure 3:
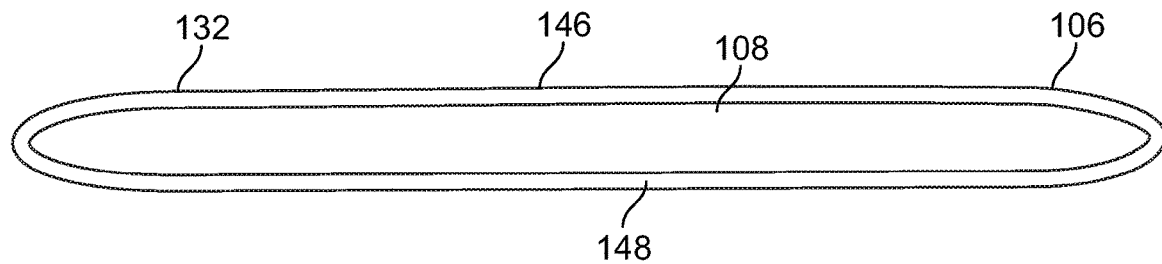
FIG. 3 is an illustration showing a diagram of a cross-sectional construction about A-A of FIG. 2, specifically depicting a two-layer woven construction in accordance with certain aspects of the present disclosure.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "implantable" refers to an ability of a medical device to be positioned at a location within a body, such as within a body lumen.

As used herein, the term "body vessel" means any tube-shaped body passage lumen that conducts fluid, including but not limited to blood vessels such as those of the human vasculature system, esophageal, intestinal, biliary, urethral and ureteral passages.

The term "branch vessel" refers to a vessel that branches off from a main vessel. The "branch vessels" of the thoracic and abdominal aorta include the celiac, inferior phrenic, superior mesenteric, lumbar, inferior mesenteric, middle sacral, middle suprarenal, renal, internal spermatic, ovarian (in the female), innominate, left carotid, and left subclavian arteries. As another example, the hypogastric artery is a branch vessel to the common iliac, which is a main vessel in this context. Thus, it should be seen that "branch vessel" and "main vessel" are relative terms.

The terms "about" or "substantially" used with reference to a quantity includes variations in the recited quantity that are equivalent to the quantity recited, such as an amount that is insubstantially different from a recited quantity for an intended purpose or function.

The term "stent" means any device or structure that adds rigidity, expansion force, or support to a prosthesis. The term "stent graft" as used herein refers to a prosthesis comprising a stent and a graft material associated therewith that forms a lumen through at least a portion of its length.

FIG. 1 is an illustration showing a top view of a tubular woven graft 102, which may be an implantable graft for implantation to a patient body. FIG. 1A is an illustration showing a magnified view of the top layer of tubular graft of FIG. 1. Referring to FIGS. 1-1A, the graft 102 may be a portion of a stent graft, and thus the graft 102 may be associated with a stent (not shown). Further, the graft 102 may be a woven graft having walls formed substantially of a woven fabric 104. The woven fabric 104 may have a plurality of warp yarns (depicted as "warp ends 130") aligned substantially in a first direction that are interwoven with a plurality of weft yarns 131 aligned substantially in a second direction, where the first direction and the second direction are substantially perpendicular. For example, the warp ends 130 may be the lengthwise threads attached to a loom before weaving begins, and may be manipulated by a reed during the weaving process. The weft yarns 131 (also known as woof or fill yarns) may be the strands that are shuttled back and forth across the warp ends 130 such that the warp ends 130 and the weft yarns 131 together define the woven fabric 104.

The graft 102 may include a main tubular section 106 and a bifurcated tubular section 110, as shown in FIG. 1. The main tubular section 106 may be configured for deployment in a vessel or other body lumen, such as an aorta of a human (or other) patient to treat an aneurysm. To allow blood flow through the main section 106, a main lumen 108 may extend through the entire tubular woven graft that is constructed in the form of woven fabric 104.

The bifurcated section 110, which also may be formed with the tubular woven fabric 104, may extend from the main section 106. In exemplary embodiment, the bifurcated section 110 may include a first branch 112 and a second branch 114 for deployment within branch vessels extending from the aorta (e.g., the iliac arteries of a human (or other) patient). The bifurcated section 110 may extend distally from the main section 106, but it may alternatively extend a different direction from the main section 106 in other embodiments. The bifurcated section 110 may include a first branch 112 and a second branch 114 (and in some embodiments, more than two branches may be included). To allow blood flow through the branches, the first branch 112 and the second branch 114 may each include a respective branch lumen 116, 118 in fluid communication with the main lumen 108 of the main section 106.

Optionally, the main section 106 may include a tapered portion 120 at its distal end 133 that extends from a cylindrical portion 132. The tapered portion 120 may be frustoconical in shape and may decrease in diameter as it extends distally from the cylindrical portion 132 of the main section 106. The tapered portion 120 may be advantageous to providing a smooth transition from the main section 106 to the bifurcated section 110. For example, when the graft 102 is configured for use in and around the aorta, the tapered portion 120 may provide a smooth transition between the abdominal aorta and the common iliac arteries, but tapers for other body locations are also contemplated. In other embodiments, the main section 106 may lack the tapered second 120, and thus the bifurcated section 110 may extend directly from the cylindrical portion 132. When the tapered portion 120 is included, it may be formed with a woven structure as described in more detail below.

Similarly, the bifurcated section 110 may include a tapered section 122 where at least one of the branches includes a tapered structure. For example, the first branch 112 may include a first branch taper 124 and the second branch may include a second branch taper 126. The first branch taper 124 and the second branch taper 126 may each include a respective frustoconical wall 128 that surrounds the branch lumens 116, 118. Advantageously, the first branch taper 124 and/or the second branch taper 126 may provide a smooth transition from a main vessel (e.g., the abdominal aorta) to smaller respective branch vessels.

FIG. 2 is an illustration depicting a diagram of a weaving orientation during formation of the graft 102. As shown, the warp ends 130 extend substantially in the longitudinal direction of the graft 102, and thus the weft threads 131 (FIG. 1A) extend substantially perpendicular to the longitudinal direction of the graft 102. The warp ends 130 in FIG. 2 are depicted as extending through the graft 102, and also beyond the limits of the graft walls (as they would appear during the weaving process prior to the graft 102 being removed from the loom).

In the bifurcated section 110 of the graft 102, certain warp ends 130 may be dropped from the graft material (e.g., free from weft threads and thus not incorporated into the woven fabric 104) in a located between the first branch 112 and the second branch 114. When the machine direction is from distal-to-proximal (as depicted in FIG. 2), the warp ends 130 may be picked up (e.g., interwoven with weft threads due to communication with the shuttle) at a junction 154 where the first branch 112 and the second branch 114 meet. A distal end of the main lumen 108 (FIG. 1) may be located at a proximal end of the junction 154.

The tapered portion 120 of the main section 106 may include a seam extension 134. The seam 134 is used to create the tapered geometry in the tubular graft. The seam extension 134 may extend outwardly from a wall of the tapered portion 120, as shown. The seam extension 134 may be defined by a location where the warp yarns forming the cylindrical portion 132 are transitioned into a single-layer woven structure (as described in more detail below with reference to FIGS. 4-8). Advantageously, and as described in more detail below, the tapered portion 120 may provide an area beyond the wall 144 of the tapered portion 120 where the warp ends 130 are locked/secured in place with respect to the weft threads such that the woven fabric 104 does not fray or otherwise unravel at a seam between upper and lower woven layers. FIG. 3 is an illustration showing a diagram of a cross-sectional construction of the cylindrical portion 132 of the main section 106 about A-A of FIG. 2. Specifically, the perspective of FIG. 3 is from a proximal viewpoint looking distally through the main lumen 108. While the cylindrical portion 132 is ovular in shape in FIG. 3, it expand into a substantially cylindrical shape once the weaving process is complete and/or upon deployment into a patient body. During weaving, the cylindrical section may be formed by a two-layer woven structure where the top woven layer forms an upper side 146 of the cylindrical portion 132 and a bottom woven layer forms a lower side 148 of the cylindrical portion. During the weaving process, to prevent closing the main lumen 108, the warp ends associated with the upper side 146 may remain only associated with the upper side 146, and the warp ends associated with the lower side 148 may remain only associated with the lower side 148. That is, the warp threads associated with the upper side 146 do not interweave with weft threads as they are forming the lower side 148, and vice versa. The resulting structure is the tubular structure with the main lumen 108 extending therethrough, where the upper side 146 and the lower side 148 each define approximately half the perimeter of the cylindrical portion 132 (although it is also contemplated that one of the upper side 146 and the lower side 148 may be substantially larger than the other).

Figure 4:
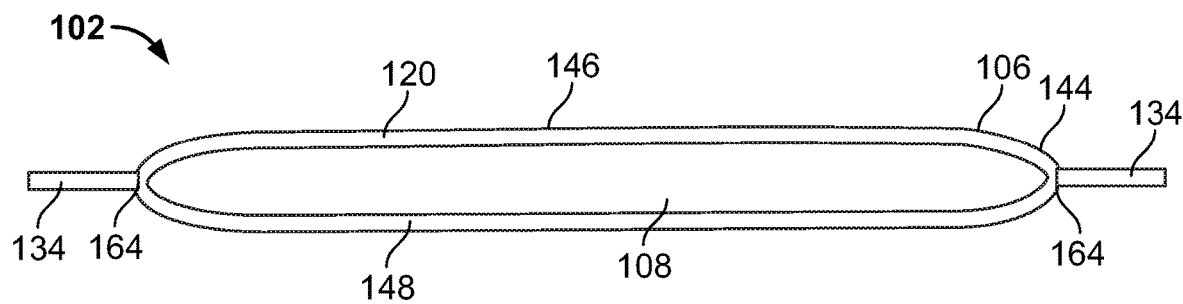
FIG. 4 is an illustration showing a diagram of a cross-sectional construction about B-B of FIG. 2, specifically showing a tapered section with a seam extension in accordance with certain aspects of the present disclosure.

FIG. 4 is an illustration showing a diagram of a cross-sectional construction of the tapered portion 120 of the main section 106 about B-B of FIG. 2. Specifically, the perspective of FIG. 4 is from a proximal viewpoint looking distally through the main lumen 108. As shown, the tapered portion 120 is formed with a two layer woven structure similar to the structure of the cylindrical portion 132 as described above (with reference to FIG. 3), but fewer warp ends may be included in the layer defining the upper side 146 and/or the layer defining the lower side 148 such that the diameter of the main lumen 108 within the tapered portion 120 of FIG. 4 is smaller than the diameter of the main lumen 108 in the cylindrical portion 132. More particularly, the diameter of the main lumen 108 may incrementally decrease as the tapered portion 120 extends distally from the cylindrical portion 132 (as shown in FIG. 2, above). The incremental decrease may be caused by incrementally decreasing the number of warp ends that are incorporated into the two layer woven structure with the upper side 146 and the lower side 148.

In the tapered portion 120, the upper side 146 and the lower side 148 may meet at a junction or seam 164. As shown in FIG. 4, two seam extensions 134 may extend outwardly from the wall 144 at the seam 164 where the upper side 146 and the lower side 148 meet. The warp ends and the weft threads in both the upper side 146 and the lower side 148 are incorporate into the woven structure of the seam extensions 134. Thus, the seam extensions 134 may have a larger density (e.g., a higher thread density or thread count) than both the upper side 146 and the lower side 148 of the tapered portion 120.

Advantageously, the seam extensions 134 capture the warp ends that are dropped from the fabric of the tapered portion 120 as its diameter changes (e.g., due to incrementally dropping warp ends along the tapered portion 120 as its diameter decreases). For example, the warp ends 130 in the seam extension 134 may be included in the area 135 of FIG. 2 where no weft threads are located, and thus without the seam extension 134, those same warp ends 130 may be relatively loose immediately adjacent to the graft wall, leaving them prone to fraying and/or otherwise compromising the structure of the wall 144 of the graft 102 at the seam 164 shown in FIG. 4. Referring to FIG. 4, by including the seam extension 134, the woven structure adjacent to the seam 164 may have enhanced durability (e.g., it may be resistant to fraying). In some embodiments, a fusible material (e.g., a yarn or strand with a suitable melting point for heat-processing) may be included in the seam extensions 134, which may be head processed at least in the seam extensions 134 to lock the warp yarns and/or the weft threads in place. The fusible material may be included with a yarn or strand (e.g., with at least one of the warp ends or weft threads), or it may be included separately (e.g., in a post-weaving manufacturing step). In some embodiments, a similar locking effect may be achieved in the seam extension 134 without (or in addition to) heat processing, such as by including an adhesive in the seam extension 134. For example, some options for yarn materials include polyethylene terephtalate (PET) or ePTFE, which may be biocompatible and/or hemocompatible. Any other suitable biocompatible and/or hemocompatible material can be used.

Figure 5:
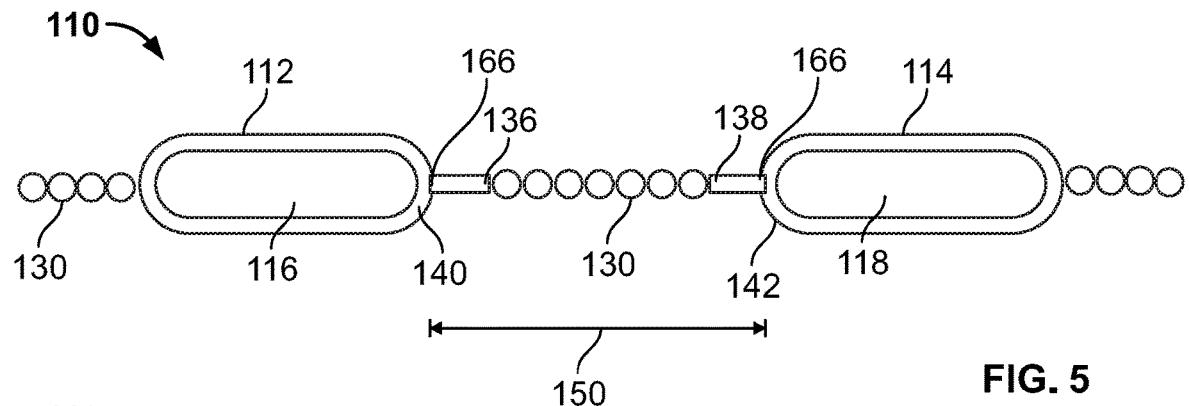
FIG. 5 is an illustration showing a diagram of a cross-sectional construction about C-C of FIG. 2, specifically showing tapered sections of branches of a bifurcated section in accordance with certain aspects of the present disclosure.

FIG. 5 is an illustration showing a diagram of a cross-sectional construction of the bifurcated section 110 about C-C of FIG. 2. Specifically, the perspective of FIG. 5 is from a proximal viewpoint looking distally through the first branch lumen 116 of the first branch 112 and the second branch lumen 118 of the second branch 114. As shown, each of the first branch 112 and the second branch 114 may be formed of a two layer woven structure similar to the two layer woven structure described above to form the cylindrical portion 132 (FIG. 3) and the tapered portion 120 (FIG. 4). However, referring to FIG. 5, a space 150 may be located between the first branch 112 and the second branch 114 where centrally-located warp ends 130 are dropped and thus not incorporated into either of the first branch 112 and the second branch 114. The space 150 between the first branch 112 and the second branch 114 may grow gradually as the first branch 112 and the second branch 114 extend away from the main section 106 (FIG. 2), and such growth may be caused by tapering at least one of the first branch 112 and the second branch 114 in a manner similar to as described above with reference to FIG. 4. If a taper is included with at least one of the branches, at least one corresponding seam extension may also be included.

For example, referring to FIG. 5, a first branch seam extension 136 may extend outwardly from a wall 140 of the first branch 112 and a second branch seam extension 138 may extend outwardly from a wall 142 of the second branch 114. The branch seam extensions 136, 138 may be formed with a single-layer woven structure where the warp ends from the two layer woven structure of the respective branch 112, 114 are incorporated into the single-layer woven structure. Like the seam extension 134 (FIG. 4) described above, the branch seam extensions 136, 138 of FIG. 5 may be advantageous for providing a space where the warp ends 130 (and/or the weft threads) are secured/locked in place to inhibit fraying along the junctions or seams 166 between an upper side and a lower side of the branches 112, 114 as they taper.

While only one seam area is shown per branch in FIG. 5, it is contemplated that each branch may include two seam areas, particularly if the branches 112, 114 taper along both seams/junctions where the upper sides and lower sides of the branches 112, 114 meet. Further, while the first branch 112 and the second branch 114 are mirror-images of each other, this is not necessarily true in all embodiments. It is contemplated that only one of the branches 112, 114 may include a seam extension (e.g., particularly if only one branch tapers), and the seam extensions 136, 138 of the branches 112, 114 do not necessarily need to be the same size.

Figure 6:
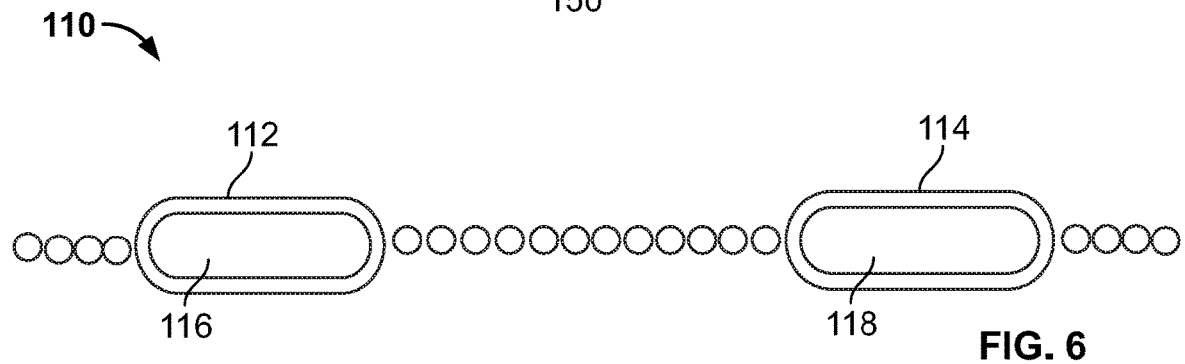
FIG. 6 is an illustration showing a diagram of a cross-sectional construction of about D-D of FIG. 2, specifically showing the bifurcated portion having branches with substantially constant diameters in accordance with certain aspects of the present disclosure.

FIG. 6 is an illustration showing a diagram of a cross-sectional construction of the bifurcated section 110 about D-D of FIG. 2. Specifically, the perspective of FIG. 6 is from a proximal viewpoint looking distally through the first branch lumen 116 of the first branch 112 and the second branch lumen 118 of the second branch 114. As shown in FIG. 6, the first branch 112 and the second branch 114 do not include a seamed area. This lack of a seamed area is due to the first branch 112 and the second branch 114 extending with a substantially constant diameter in this location, and therefore a seamed area at this location may not be necessary since no warp ends are dropped at this location from the respective two-layer woven structures forming the tubular branches as they are woven in a shuttle weaving machine as explained earlier.

Figure 7:
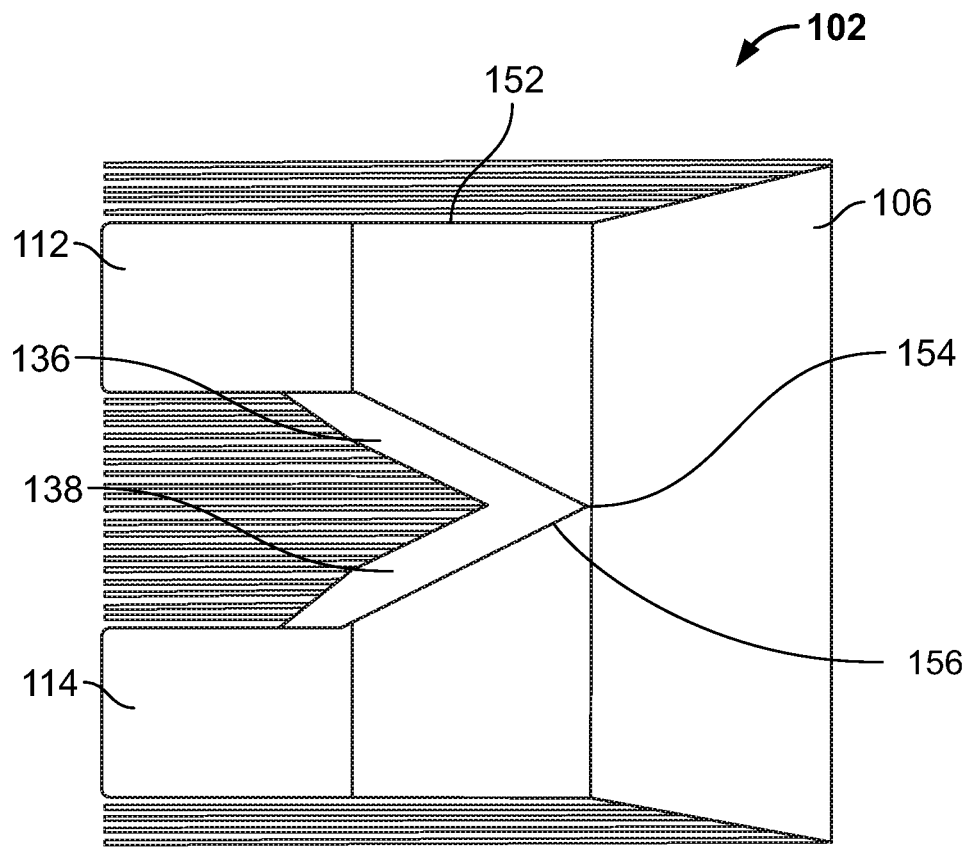
FIG. 7 is an illustration showing a close-up view of a proximal portion of the bifurcated section of the graft, specifically showing a common seam extension between two branches in accordance with certain aspects of the present disclosure.

FIG. 7 is an illustration showing a close-up view of the proximal portion 152 of the bifurcated section of the graft 102. As shown, the first branch seam extension 136 of the first branch 112 and the second branch seam extension 138 of the second branch may meet at a branch junction 154 (i.e., the location where the first branch 112 and the second branch 114 meet). Within a distal junction area, a common seam extension 156 may exist, and therefore no warp ends may be unused between the first branch 112 and the second branch 114 in the junction 154. The common seam extension 156 may extend to the main section 106.

Figure 8:
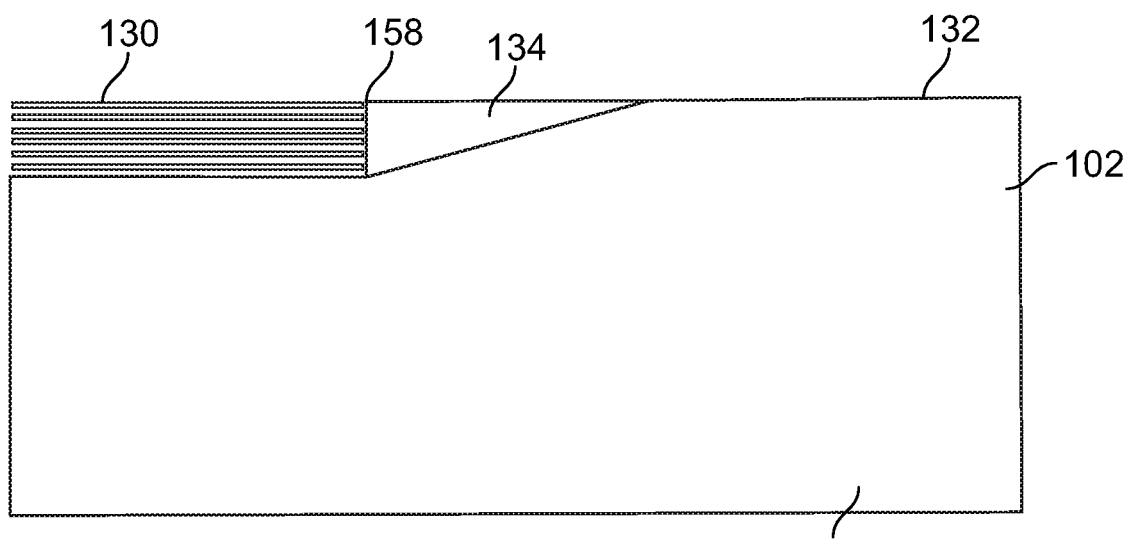
FIG. 8 is an illustration showing a shaped embodiment of a seam extension in accordance with certain aspects of the present disclosure.

Seamed areas such as those described above may have any one of a variety of shapes. Certain examples are shown in the illustrations of FIGS. 8-11. While the following examples reference the seam extension 134 (e.g., of the main section 106), similar and/or identical shapes may be used for the branch seamed areas 136, 138 (see FIG. 5). One example is shown in FIG. 8, where a seam extension 134 has a rectangular shape at its distal end 158. Such a shape may be formed where the warp ends 130 are dropped from the distal end at the same time during weaving, and/or such that each of the dropped warp ends 130 enter the seam extension 134 at a common weft thread.

Figure 9:
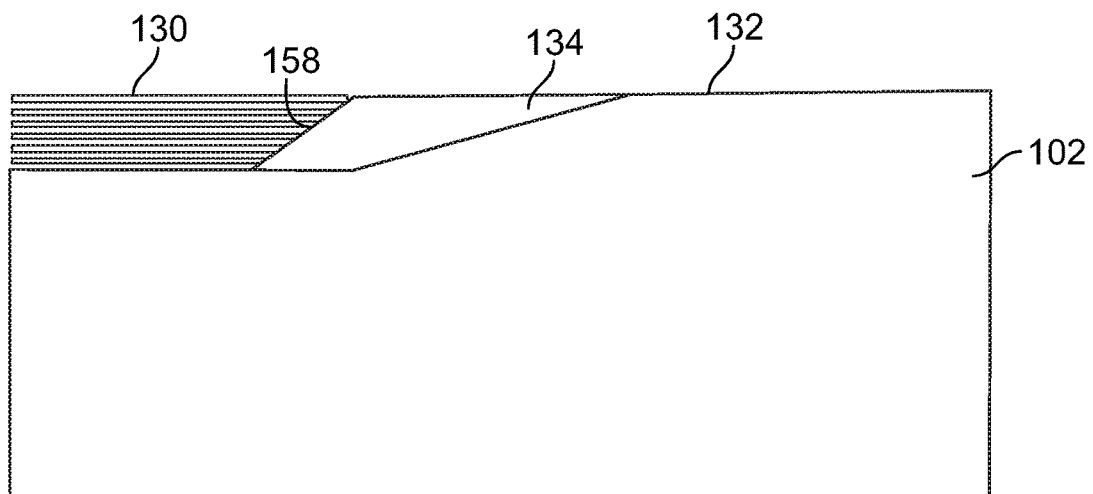
FIG. 9 is an illustration showing another shaped embodiment of a seam extension in accordance with certain aspects of the present disclosure.

FIG. 9 shows another potential shape of the seam extension 134. In FIG. 9, the seam extension 134 includes a slanted shape at its distal end 158, which may be formed by dropping the warp ends 130 gradually. For example, if weaving in the proximal direction (i.e., from distal-to-proximal), each successive shuttle motion during weaving may pick up an additional warp end 130 that was previously unused until reaching a warp end 130 that will eventually form the outer edge 160 of the main section 106.

Figure 10:
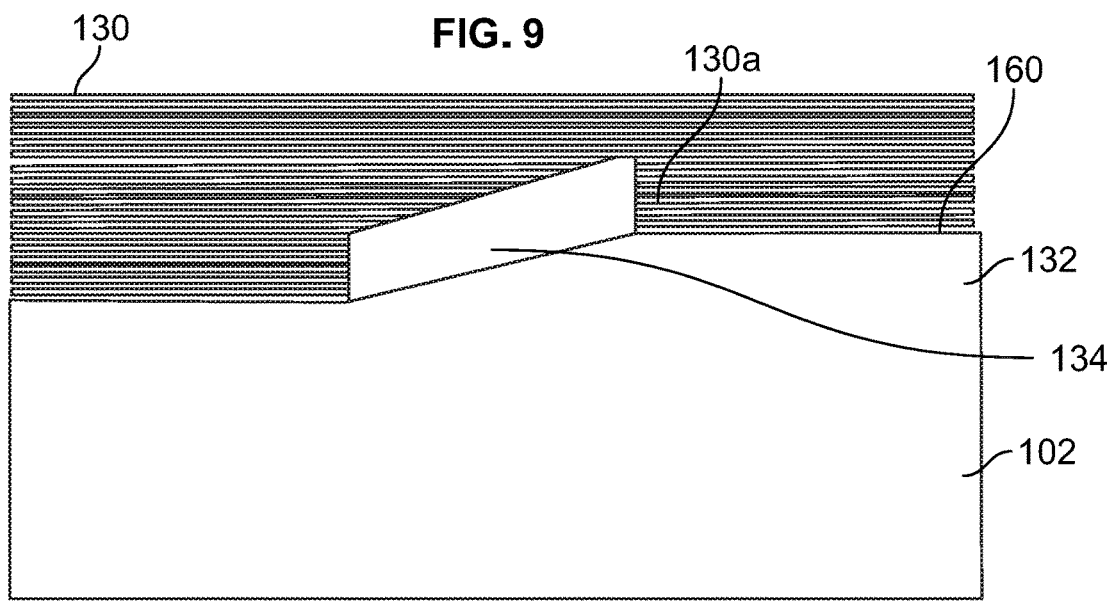
FIG. 10 is an illustration showing another shaped embodiment of a seam extension in accordance with certain aspects of the present disclosure.
Figure 11:
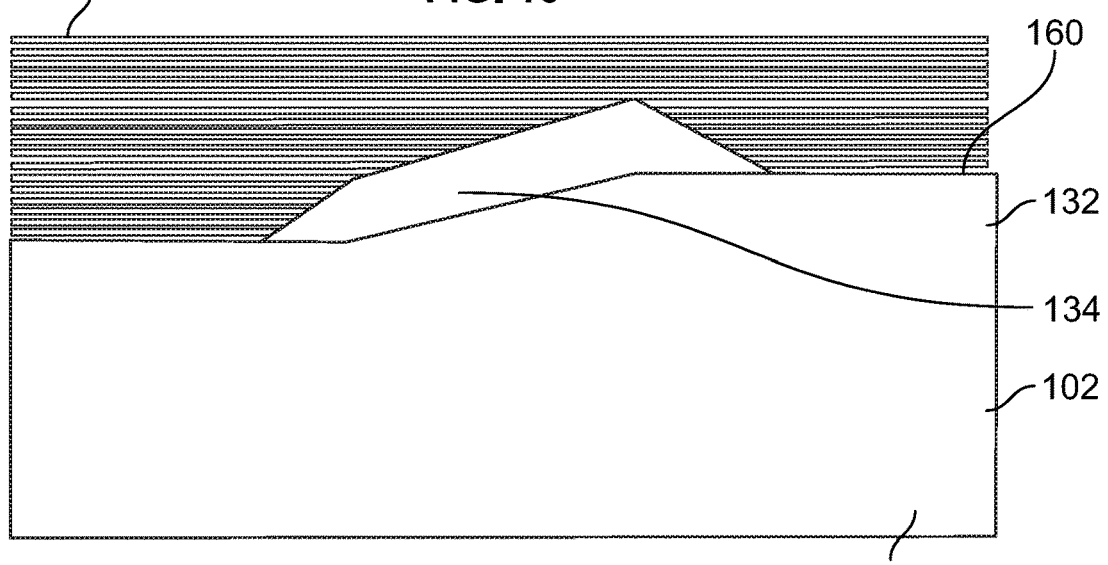
FIG. 11 is an illustration showing another shaped embodiment of a seam extension in accordance with certain aspects of the present disclosure.

In FIG. 10, the depicted seam extension 134 extends beyond the outer edge 160 of the cylindrical portion 132 of the graft 102. Thus, some of the warp ends 130 used in the seam extension 134 may not be used elsewhere in the graft 102. To illustrate, the warp end 130a of FIG. 10 may be picked up by the seam extension 134 at the proximal end of the seam extension 134 and dropped at the distal end of the seam extension 134, but it may be free from the woven material of the graft 102 at locations proximal of the seam extension 134 and also at locations distal of the seamed area. FIG. 11 depicts the seam extension 134 as also extending beyond the outer edge 160 of the cylindrical portion 132 of the graft 102, but with slanted edges rather than the squared edges as shown in FIG. 10.

Figure 12:
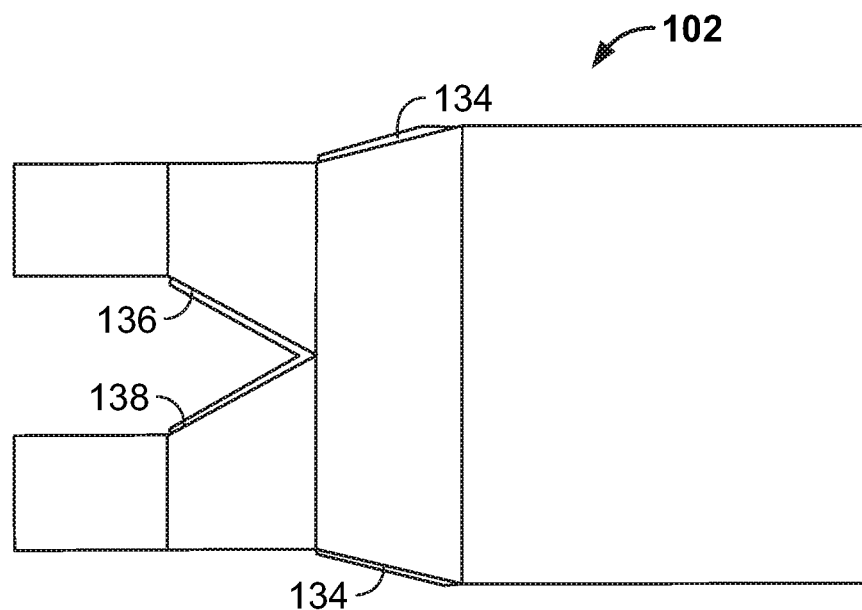
FIG. 12 is an illustration showing a graft having trimmed seam extensions and trimmed branch seam extensions in accordance with certain embodiments of the present disclosure.

FIG. 12 is an illustration showing the graft 102 having trimmed seam extensions 134 and branch seam extensions 136, 138. For example, the seam extensions 134 may initially be relatively wide (e.g., have a relatively large dimension extending outwardly from the wall of the graft 102) such that the warp ends and/or the weft threads remain relatively secure after the weaving process. Advantageously, the structure of the graft 102 may be retained even prior to a fusing or other securement process post-weaving. After weaving, the seam extensions 134 may be secured (e.g., fused) as described above. Once secured, the relatively large width of the seam extensions 134 may no longer be necessary, so they may be trimmed. The trimming process may include cutting the seam extensions 134 with scissors, a knife, a punch, or any other suitable cutting device, and it may be performed manually by a manufacturing professional or automatically with the use of a machine. Advantageously, by trimming the seam extensions 134, it may be ensured that the seam extensions 134 do not irritate or damage a body surface (e.g., an inner diameter surface of an artery), do not inhibit deployment of the graft 102, etc.

Figure 13:
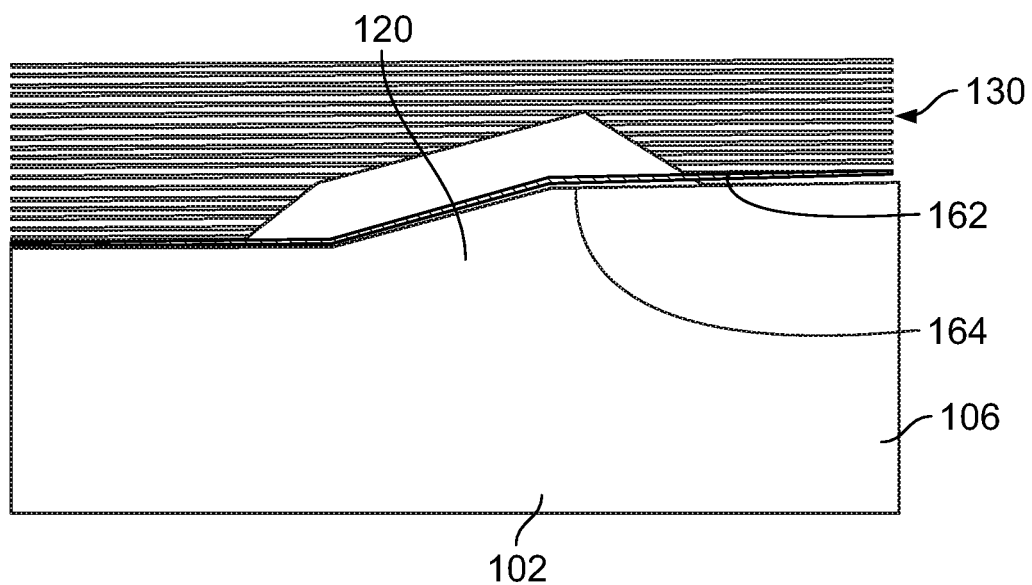
FIG. 13 is an illustration showing a graft having a meltable yarn extending along a seam of a taper in accordance with certain aspects of the present disclosure.

FIG. 13 is an illustration showing the graft 102 having a meltable yarn 162 that extends along the seam 164 of the graft 102. When no tapers are included in the graft 102, the meltable yarn 162 may simply be a warp end 130 having a particular material, but in exemplary embodiments the warp end 130 is included along the seam 164 of the tapered portion 120, and thus the meltable yarn 162 may extend diagonally with respect to the warp ends 130 (at least in the tapered portion 120). To include the meltable yarn 162, the weaving machine that manufactures the graft 102 may include an open reed. The meltable yarn 162 can therefore be independently manipulated relative to the warp ends 130 and placed along the seam 164, as desired.

The meltable yarn 162 may include any suitable material, such as a thermoplastic polymer material having a melting point configured to fuse when heat processed. That is, a material of the meltable yarn 162 may at least partially melt when heated and then solidify when later cooled to enhance the structure of the seam 164. For example, the meltable yarn 162 may be a yarn including a low melting polyester or other bio and hemocompatible thermoplastic with a melting point lower than the melting point of base material from which the body of the graft is constructed. For example, the melting point of the meltable yarn 162 may be about 200 degrees Celsius or less, such as less than about 180 degrees Celsius. In addition, any other irreversibly meltable/fusible polymeric or natural yarn can be used for this purpose. Advantageously, the meltable yarn 162 can be heat-processed after the weaving process to seal/secure the woven threads along the structure of the seam 164 to enhance the strength and durability of the graft 102. While only one strand of the meltable yarn 162 is depicted, it is contemplated that a plurality of meltable yarns 162 may be included together and/or separately.

Figure 14:
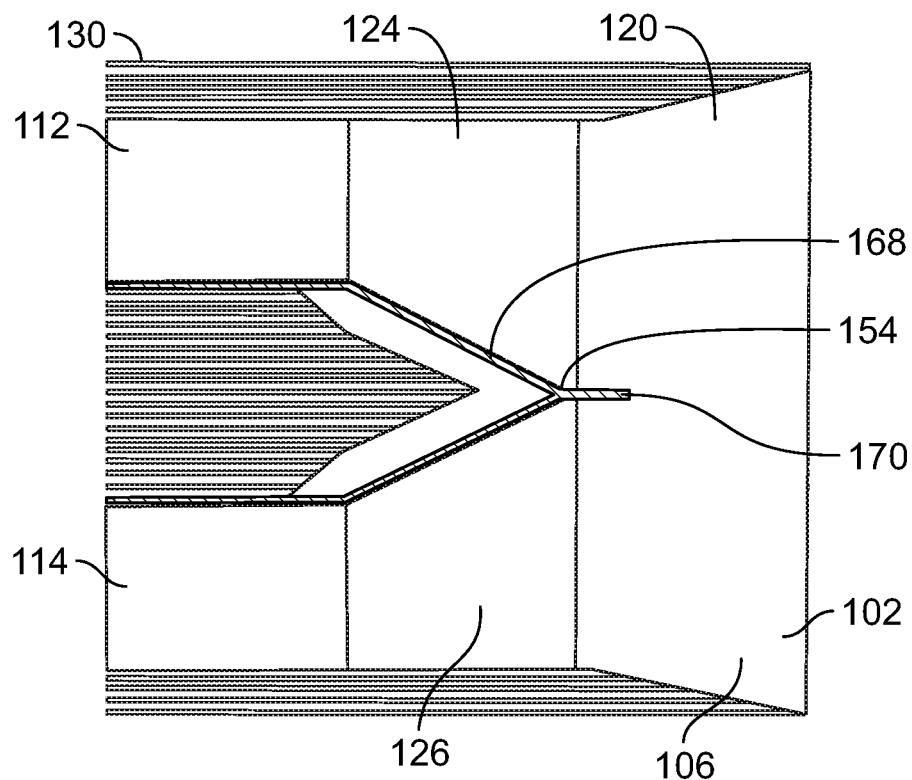
FIG. 14 is an illustration depicting a graft having a meltable yarn extending along branch tapers of a bifurcated section in accordance with certain aspects of the present disclosure.

FIG. 14 is an illustration showing the graft 102 where optional meltable yarns 168 extend along the first branch 112 and the second branch 114, including along the first branch taper 124 and the second branch taper 126. The meltable yarns 168 may include any of the aspects described above with reference to the meltable yarn 162. In FIG. 14, the meltable yarns 168 are shown as terminating at a location 170 that is just proximal of the junction 154. The meltable yarn is part of the top warp yarn layers but not interwoven into the top layer of the graft 106 until location 170. Alternatively, the meltable yarn can be fed to the weaving zone as an external yarn using a separate bobbin and then can be interwoven with the base material staring from point 170 using an open reed weaving procedure.

Figure 15:
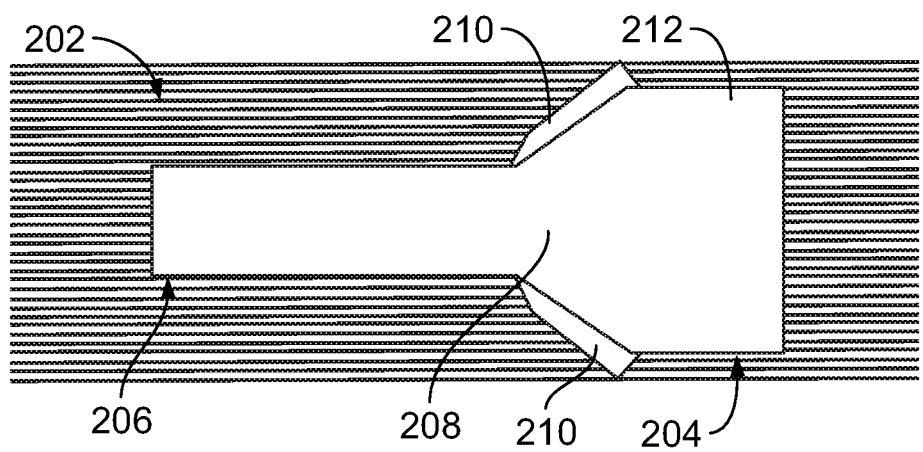
FIG. 15 is an illustration showing a graft having a first tubular section and a second tubular section with a tapered section therebetween, where the tapered section has seam extensions in accordance with certain aspects of the present disclosure.

The aspects and features described above may also apply to grafts having different shapes, and many graft shapes are contemplated. For example, one geometry of an iliac leg graft 202 is shown in FIG. 15, which is formed of a woven fabric 212. The graft 202 may lack a bifurcated section, but otherwise may be similar to the graft 102 described above. Referring to FIG. 15, the graft 202 may have a first tubular section 204 and a second tubular section 206, where the second tubular section 206 has a smaller diameter than the first tubular section 204. A tapered section 208 may be located between the first tubular section 204 and the second tubular section 206. Like the embodiments described above, a seam extension 210 may be located on each side of the tapered section 208. The seam extension 210 may incorporate any of the features and aspects described with respect to the seam extensions discussed above.

While the present invention has been described in terms of preferred embodiments, it will be understood, of course, that the invention is not limited thereto since modifications may be made to those skilled in the art, particularly in light of the foregoing teachings.

We claim:

1. An implantable graft, comprising:
a main section having walls formed with a woven fabric, the main section having a main lumen extending therethrough; and
a bifurcated section having walls formed with the woven fabric, wherein the bifurcated section extends from main section, wherein the bifurcated section includes a first branch and a second branch, and wherein the first branch and the second branch each include a branch lumen in fluid communication with the main lumen,
wherein at least one branch of the bifurcated section includes a branch taper formed by a seam connecting a first woven layer and a second woven layer, and
wherein a seam extension extends outwardly along the seam of the branch taper, the seam extension being a single-layer woven structure, and the single-layer woven structure comprising at least two adjacent warp ends woven with at least two adjacent weft threads.

2. The graft of claim 1, wherein the seam extension includes a warp end that is included in one of the first woven layer and the second woven layer in the main section, and wherein the warp end exits the graft at the seam extension.

3. The graft of claim 1, wherein the seam extension includes at least one weft thread that forms the first woven layer in the at least one branch and also at least one weft thread that forms the second woven layer in the at least one branch.

4. The graft of claim 1, wherein the seam extension includes at least one warp end that forms the first woven layer in the main section and also at least one warp end that forms the second woven layer in the main section.

5. The graft of claim 1, wherein the seam extension includes a meltable yarn having a melting point that is lower than a melting point of at least one warp end and at least one weft yarn.

6. The graft of claim 5, wherein a portion of the meltable yarn extends diagonally relative to warp ends of the woven fabric.

7. The graft of claim 1, wherein the seam extension has a higher thread density than both the first woven layer and the second woven layer in the at least one branch.

8. The graft of claim 1, wherein the seam extension is trimmed.

9. The graft of claim 1, wherein the seam extension includes at least one warp end that is excluded from the main section.

10. An implantable graft, comprising:
a woven fabric forming walls of a first tubular section and a second section, the first tubular section having a first diameter and the second section having a smaller second diameter;
a tapered section located between the first tubular section and the second section, wherein the tapered section decreases in diameter as it extends from the first tubular section to the second section; and
a seam extension extending from a seam of the tapered section, wherein the seam joins a first woven layer of the tapered section to a second woven layer of the tapered section, and wherein the seam extension includes a single-layer woven structure, and the single-layer woven structure comprising at least two adjacent warp ends woven with at least two adjacent weft threads.

11. The graft of claim 10, wherein the seam extension includes a warp end that is included in one of the first woven layer and the second woven layer in the first tubular section, and wherein the warp end exits the graft at the seam extension.

12. The graft of claim 10, wherein the seam extension includes at least one weft thread that forms the first woven layer in the tapered section and also at least one weft yarn that forms the second woven layer in the tapered section.

13. The graft of claim 10, wherein the seam extension includes at least one warp end that forms the first woven layer in the first tubular section and also at least one warp end that forms the second woven layer in the first tubular section.

14. The graft of claim 10, wherein the seam extension includes a meltable yarn having a melting point that is lower than a melting point of at least one warp end and at least one weft yarn.

15. The graft of claim 14, wherein a portion of the meltable yarn extends diagonally relative to warp ends of the woven fabric.

16. The graft of claim 10, wherein the seam extension has a higher thread density than both the first woven layer and the second woven layer.

17. The graft of claim 10, wherein the seam extension is trimmed.

18. The graft of claim 10, wherein the seam extension includes at least one warp end that is excluded from the first tubular section.

19. The graft of claim 10, wherein the second section includes at least two branches.

20. An implantable graft, comprising:
a woven fabric forming walls of a first tubular section and a second section, the first tubular section having a first diameter and the second section having a smaller second diameter;
a tapered section located between the first tubular section and the second section, wherein the tapered section decreases in diameter as it extends from the first tubular section to the second section; and
a seam extension extending from a seam of the tapered section, wherein the seam joins a first woven layer of the tapered section to a second woven layer of the tapered section, and wherein the seam extension includes a single-layer woven structure,
wherein the seam extension includes a meltable yarn having a melting point that is lower than a melting point of at least one warp end and at least one weft yarn.

* * * * *